United States Patent [19]
Yamamoto et al.

[11] Patent Number: 4,474,883
[45] Date of Patent: Oct. 2, 1984

[54] PROCESS FOR SACCHARIFICATION OF ROOTSTOCKS AND SUBSEQUENT ALCOHOL FERMENTATION

[75] Inventors: Takehiko Yamamoto, Izumi; Michihiko Nojiri, Takaishi; Kazuo Kakutani, Nishinomiya; Yoshikazu Matsumura, Nara; Shozo Ito, Ohsaka, all of Japan

[73] Assignees: Mitsui Engineering & Shipbuilding Co., Ltd., Tokyo; Ueda Chemical Industrial Co. Ltd.; Hankyo Kyoei Bussan Co., Ltd., both of Ohsaka, all of Japan

[21] Appl. No.: 349,859

[22] Filed: Feb. 18, 1982

[30] Foreign Application Priority Data

Mar. 14, 1981 [JP] Japan ................................. 56-36762

[51] Int. Cl.$^3$ ............................................. C12P 7/14
[52] U.S. Cl. ................................... 435/162; 435/163
[58] Field of Search ........................... 435/99, 161–163

[56] References Cited
U.S. PATENT DOCUMENTS 4,247,638  1/1981  Müller et al. ....................... 435/99
4,316,956  2/1982  Lützen ............................... 435/99 X

FOREIGN PATENT DOCUMENTS 2089836  6/1982  United Kingdom ................ 435/161

Primary Examiner—Ferris H. Lander
Attorney, Agent, or Firm—Beall Law Offices

[57] ABSTRACT

For saving the heat energy required for alcohol production, processes are provided for subjecting rootstocks (Rhizomes) to enzymatic hydrolysis without conventional cooking with steam in order to obtain a high concentration saccharified material which is then subjected to alcohol fermentation.

The first process comprises dipping raw rootstocks in a dilute acid for the purpose of sterilization, then crushing the sterilized rootstocks, macerating the crushed rootstocks, dextrinizing the macerated material by the action of bacterial α-amylase and adding to the dextrinized material glucoamylase and yeast for alcohol fermentation to effect saccharification thereof and subsequent alcohol fermentation.

The second process comprises sterilizing rootstocks with a dilute acid and then crushing it, followed by adding blended maceration enzymes to effect maceration amd saccharification with subsequent alcohol fermentation by yeast.

34 Claims, No Drawings

PROCESS FOR SACCHARIFICATION OF ROOTSTOCKS AND SUBSEQUENT ALCOHOL FERMENTATION

BACKGROUND OF THE INVENTION

1. Field of the Invention

This invention relates to a process for saccharification of rootstocks and subsequent alcohol fermentation. More particularly it relates to a process for saccharifying rootstocks such as sweet potatoes, cassave roots and white potatoes according to an enzymatic processing without conventional steaming, and using the resulting material as a feed substrate for alcohol fermentation.

2. Description of the Prior Art

Fossil energy resources have been getting scarcer, and as a countermeasure to this, conversion of renewable resources i.e. biomass into energy resources and utilization of biomass as chemical raw materials have recently come to public notice.

Heretofore, according to conventional processes for saccharification of rootstocks such as sweet potatoes. Cassava roots, white potatoes, etc. and subsequent alcohol fermentation, such raw materials have been once cooked for gelatinization of starch followed by adding α-amylase to act on the gelatinized starch to convert it into dextrin, which, in turn, has been subjected to alcohol fermentation.

However, such conventional processes have had drawbacks in that large scale equipments such as high pressure cookers have been required and also a large quantity of heat has been needed for cooking. In particular, such a quantity of heat and that required for distilling off ethanol from the fermented beer for alcohol has increased the amount of heat required for the overall process of ethanol fermentation, whereby no commercially effective process could have been achieved. For example, conventional cooking of rootstocks to gelatinize starch for saccharification proceeding to subsequent alcohol fermentation has been carried out under pressure of about 2.5 kg/cm$^2$ for about 30 to 60 minutes and the quantity of steam required for the heating has amounted to about 30% of the total quantity of steam required for alcohol production. Further, drain mixes in the material during the cooking treatment, whereby the feed substrate for alcohol is diluted to reduce the concentration of the alcohol obtained by fermentation. Furthermore, a quantity of heat required for alcohol distillation carried out in the final step is increased and the yield of the product alcohol per unit of a quantity of heat is reduced. According to the conventional processes, the heat energy required for the alcohol distillation has amounted to as large as ½ of the combustion energy of the alcohol.

SUMMARY OF THE INVENTION

An object of the present invention is to provide a process of subjecting rootstocks to enzymolysis without conventional cooking, to obtain a high concentration of a saccharified material, which is then subjected to alcohol fermentation at high concentration.

Another object of the present invention is to provide a process for saving the heat energy required for alcohol distillation.

Other objects of the present invention will be apparent from the following description.

In order to attain the above-mentioned objects, the present inventors first have noted that the object of conventional cooking of rootstocks has consisted not only in gelatinization of starch, but in sterilization of rootstocks so that contamination by microbes should not occur during alcohol fermentation, and have made studies on a process of carrying out the sterilization of raw material rootstocks separately from the gelatinization and saccharification. As a result, it has been found that if rootstocks are washed with water to remove attached soil and immersed in a dilute acid at room temperature for several hours, it is possible to sterilize microorganisms which are harmful for alcohol fermentation. Further, they have made studies on saccharification of starch, and found that if maceration enzymes are first applied to the crushed rootstocks to form a slurry, and liquefying α-amylase is then added to the slurry followed by slightly warming for dextrinization of starch, saccharification by glucoamylase is notably enhanced, and that particularly when white potatoes are used as raw material and a portion of the whole of the supernatant liquid of the macerated material formed by the action of maceration enzymes is removed, followed by the treatment with a bacterial α-amylase, then a system of high concentration of alcohol fermentation can be achieved.

The first process of the present invention has been completed based on the above-mentioned findings, which process comprises:

Sterilizing rootstocks through immersion treatment in a dilute acid,

Crushing the sterilized rootstocks,

Macerating the crushed rootstock to slurry by enzymes.

Adding bacterial α-amylase to the slurry followed by warming to dextrinize the starch.

Adding to the dextrinized material glucoamylase and yeast for alcohol fermentation to effect alcohol fermentation in parallel with saccharification, thereby producing a high concentration of alcohol at high rate.

The second process of the present invention comprises sterilizing rootstocks through immersion treatment in a dilute acid and then crushing them as in the first process, followed by macerating the tissue of the rootstocks by blended maceration enzymes and saccharifying starch contained in the macerated material by the action of glucoamylase, and subjecting the resulting material to alcohol fermentation.

In the first process of the present invention, since the dextrinization process is employed that is carried out at relatively high temperature such as 80°-90° C. adding bacterial α-amylase, the whole reaction becomes rapid. In the second process, which is carried out without dextrinization and under a mild temperature conditions in the range of 20°-45° C. using the blended enzymes for maceration of the tissue of the root stocks and glucoamylase to saccharify raw starch, the reaction is not so rapid, but the energy for temperature elevation as needed in the case of the first process is saved.

DESCRIPTION OF THE PREFERRED EMBODIMENTS

In the processes of the present invention, rootstocks used as a raw material are preferably selected from sweet potatoes, cassava roots ad white potatoes which are available in a large amount. Such root-stocks are washed to remove soil and sand attached thereto, followed by immersing them in a dilute acid solution. As for the acid, not only mineral acids such as hydrochloric acid, sulfuric acid, nitric acid, but organic acids such as acetic acid may be used. The concentration of the acid is preferably in the range of 0.02 to 0.08N (Normality) in the case of mineral acids, and 0.04 to 0.10N in the case of acetic acid. The pH of the acid solution is preferably in the range of 1.6 to 2.8. The immersion time required is about 4 hours or longer, preferably 6 hours or longer, at room temperature. That acid treatment makes it possible to sterilize the microbes adhered to root-stocks, which are harmful to alcohol fermentation.

Unless the above-mentioned acid immersion treatment is carried out, an unfavorable acid fermentation such as a lactic acid fermentation is liable to occur due to bacteria adhered to rootstocks. For example, when sweet potatoes were washed only with water without acid immersion, crushed and just thereafter subjected to the action of maceration enzymes, followed by adding bacterial α-amylase to the macerated material to dextrinize the starch contained therein, adding saccharogenic enzyme and yeast for alcohol fermentation, and subjecting the mixture to fermentation, then lactic acid fermentation due to the action of contaminated microbes occurred and considerably retarded alcohol fermentation. Further, in another example, not only lactic acid fermentation but butyric acid fermentation occurred, which notably reduced the yield of alcohol.

Crushing of rootstocks is carried out in order to make it easily subject to the action of maceration enzymes. It may be carried out by means of such a machine as a disposer, a mincer, a slicer, a dispersion mill, etc. The crushing treatment is preferably carried out as sterilely as possible. Rootstocks are preferably crushed into as fine particles as possible, for example, those of about 8 to 20 meshes on the average. The maceration enzymes may be added either when rootstocks are crushed or thereafter.

The maceration enzymes are composed mainly of polygalacturonase such as pectin endopolygalacturonase and contain small amounts of carboxymethylcellulase, arabinoxylanase and arabinogalactanase. As for commercially available products of such enzymes, "Cellulosin AC" and "Orienzyme B" (tradenames of products made by Ueda Chemical Industrial Co., Ltd., Japan) are mentioned.

In place of the enzyme agents for macerating the crushed rootstocks, Koji of molds producing the maceration enzymes may be used. Such Koji contains mainly pectic enzymes containing a large amount of pectin endopolygalacturonase. Its amount to be added is preferably 50 to 1,000 units in terms of pectin endopolygalacturonase per 100 g of rootstocks.

The crushed rootstocks in a suitable reaction vessel are incubated with the maceration enzymes at pH of 3.5 to 4.5, at a temperature of 20° to 45° C. for 0.5 to 1 hour. The maceration reaction may be carried out either batchwisely or continuously. The amount of the maceration enzymes or Koji of molds to be added may be 50 to 1,000 units per 100 g of rootstocks in the case of sweet potatoes, and 1/5 to 1/10 of the above-mentioned units in the case of white potatoes or cassava roots.

Bacterial α-amylase is then added to the macerated material obtained by the macerating reaction in order to dextrinize the starch contained in the material. This step is carried out by adjusting the pH of the macerated material to about 5 or higher, and then heating it at temperature of 80° to 90° C., and for about 15 minutes in the case of 80° C. and 1 to 3 minutes in the case of 90° C. The amount of the bacterial α-amylase for this processing may be 4 to 16 units per 1 g of starch in terms of starch liquefying activity, and the extent of the dextrinization is preferably between 5 and 12% in terms of the reducing sugar forming degree. The dextrinization reaction may be carried out either batchwisely or continuously. The addition step of the bacterial α-amylase is necesary in the case of white potatoes as a raw material, but it is not always necessary in the case of cassava roots or sweet potatoes unless the high rate fermentation is desired. In addition, in the case of white potatoes which starch content is low, if the supernatant liquid of the macerated material formed by the action of the macerating enzymes is removed before dextrinization by the bacteria α-amylase, it is possible to obtain such a higher concentration of alcohol as elevated as much as that corresponding to the amount of the supernatant liquid removed, in the subsequent alcohol fermentation.

The resulting liquid formed by the dextrinization is cooled and then subjected to alcohol fermentation in a conventional manner. Namely, to the dextrinized material are added saccharifying amylase (glucoamylase), yeast seed for alcohol fermentation and if necessary nutrients for the yeast depending on the kind of rootstocks, followed by fermentation under conditions of e.g. 25° C. and pH of 4.5. The saccharifying enzyme may be commercially available, liquid or powdery glucoamylase, and its amount to be added may be 2 to 10 units per 1 g of starch contained in the raw material. The fermenting yeast may be any yeast for alcohol fermentation, for Sake making or for bread baking. Further, it is also possible to use a yeast of Pichia genus effecting alcohol fermentation even at 30° C. or higher. In the alcohol fermentation, it is preferable to add small amounts of ammonium sulfate, potassium dihydrogen phosphate, calcium chloride, magnesium sulfate, etc. as nutrients for the yeast.

The blended maceration enzyme agent used in the second process contains pectin endopolygalacturonase, cellulase, hemicellulase, glycoamylase and acidically active α-amylase. The contents of the respective enzymes in the enzyme agent has no particular limitation, but it preferably consists of 300 units or more of carboxymethylcellulase (CMC) as the cellulase per 1 kg of rootstocks (one unit: an enzymatic activity by which reducing sugar corresponding to 1$\mu$ mole of glucose is freed at 40° C., at pH 4.2 in one minute when CMC is used as a substrate); 100 units or more of arabinoxylanase as the hemicellulase (one unit: an enzymatic activity by which reducing sugar corresponding to 1$\mu$ mole of xylose is formed at 40° C. in one minute when arabinoxylan of rice straw is used as a substrate); and 100 units or more of arabinogalactanase (one unit: an enzymatic activity by which reducing sugar corresponding to 1$\mu$ mole of galactose is formed at 40° C., pH 5 in one minute when arabinogalactanase of soybean seed coat is used as a substrate); 400 units or more of polygalacturonase in terms of a pectin viscosity reduction activity (one unit: an enzymatic activity by which, when the polygalacturonase is incubated with 10 ml of a 1.0% citrous pectin solution, the viscosity is reduced down to its half at 40° C., at pH 3.6 in 10 minutes); 1,500 units or more of glucoamylase in terms of a starch saccharifying activity (one unit 1$\mu$ mole of glucose is formed at 40° C., at pH 5 in one minute); and 20 units or more of acidically active α-amylase in terms of a starchdextrinizing activity determined by iodometry (one unit: an enzyme activity by which, when the α-amylase is incubated with 10 ml of a 1% soluble starch at pH 4.0, its color is reduced down to a half at 40° C. in one minute). As for the amounts of the above-mentioned respective enzymes used, although considerably larger amounts than those of the above lower limits may be employed without any obstacles, excess amounts are uneconomical; hence usually the respective upper limits are preferred to be about 6,000 units of cellulase, about 4,000 units of hemicellulase (about 2,000 units of arabinogalactanase and about 2,000 units of arabinoxylanase), about 8,000 units of polygaracturonase, about 30,000 units of gluycoamylase and about 400 units of acidically active α-amylase. The above blended enzyme agents may be usually prepared by adequately blending individual commercially available enzymes, and the respective enzymes may be preferably those of microorganism origin, such as cellulase, hemicellulase, polygalacturonase and acidically active α-amylase, produced by fungi belonging to Aspergillus genus, such as *Aspergillus niger*, glucoamylase produced by fungi belonging to Aspergillus genus such as *Aspergillus niger* or Rhizopus genus, etc. They may be those produced by molds related to the above species and in the form of liquid enzyme agents. In particular, since blended enzyme agents which have so far been known as vegetable tissue degrading enzymes (maceration enzymes) contain cellulase, hemicellulase, polygaracturonase and acidically active α-amylase almost similar to those in the blended enzyme agents used in the present invention it is possible to prepare suitable blended enzyme agents by blending glucoamylase to the above maceration enzymes and if necessary, further adding insufficient enzymes such as hemicellulase, pectinase, etc.

The maceration and saccharification treatment of rootstocks by the above blended enzyme agents is preferably carried out by contacting the sterilized rootstocks with the blended enzyme agents at pH of 3.5 to 5.0 and at temperature of 20° to 45° C., preferably of 20° to 35° C. Control of the pH is not always necessary, since sterilization of rootstocks with acid usually brings about the above mentioned pH range, but, if necessary, suitable mineral acid or alkali e.g. sodium hydroxide may be added for pH control in the treatment. The above temperature condition is the optimum one (up to about 55° C.) for enzymes, and within the above range, higher temperature can afford more shortened reaction time. Further, the above contact is sufficiently carried out merely by feeding crushed rootstocks together with the blended enzyme agents into a suitable vessel provided with or without stirring means. The reaction in the vessel may be carried out either batchwisely or continuously, and in the case of continuous operation, it is suitable to carry out the operation by adding water so as to give a dilution of about 0.1 to 0.5 to thereby facilitate continuous feeding of raw material and continuous recovery of products.

Thus the above contact makes it possible to saccharify substantially all of the starch contained in the raw materials for 7 days (168 hours), for example, in the case without application of bacterial α-amylase of the second process, and for 36 hours, for example, in the case of the first process where α-amylase is applied for dextrinizing starch. The period of time required for the saccharification varies depending on the kind of raw materials to be used, the blending ratio of the enzyme agents and their amounts used, and the reaction conditions (temperatures, pH, etc.), but, since the saccharification of starch by the enzyme agents also proceeds in the subsequent alcohol fermentaion step, it may be sufficient if the above saccharification reaction through the contact proceeds so as to effect about 50% of the theoretically calculated value of reducing activity corresponding to that of glucose.

While the macerated and saccharified material obtained in the saccharification step may be utilized as sugars for various food industries, it is particularly suitable as a raw material for alcohol fermentaion such as ethanol or propanol fermentation. Alcohol fermentation by the use of the saccharified material as a raw material may be carried out in a conventional manner, that is, by adding a yeast seed for alcohol fermentation and inorganic nutrients for the yeast to the saccharified material and maintaining the mixture under suitable temperature and pH conditions for a few days to effect a good fermentation. The resulting fermented beer is then subjected to distillation.

The above alcohol fermentation step can be carried together with the above maceration and saccharification steps. In this case, the above blended enzyme agents and yeast seed for alcohol fermentation together with inorganic nutrients therefore can be at the same time added to the crushed raw material to thereby carry out the maceration of the tissue, the saccharification of the starch and at the same time, the fermentation of the resulting sugars by the yeast, within a single system.

According to the processes of the present invention, root-stocks are washed and sterilized with a dilute acid, followed by applying specified enzyme agents to the resulting material without any cooking process, whereby it is possible to effect the maceration and saccharification easily and yet with a high yield of glucose. Further, the saccharified material is subjected to alcohol fermentaion whereby it is possible to produce a high concentration of alcohol and economize the energy required for the alcohol production. The above effects are considered to be due to the fact that the raw material is sterilized by a dilute acid in place of conventional cooking, and specified enzyme agents decompose cementing substances such as pectic substances and some cellulosic and hemicellulosic materials surrounding starch granules in the potato tissue, whereby substantially all of the starch particles are very easily saccharified by the action of glucoamylase.

The processes of the present invention will be concretely mentioned below by way of Examples. Examples 1 and 2 are directed to the above first process, and Examples 3 to 6 are directed to the above second process.

EXAMPLE 1

Two kg of sweet potato washed with water in advance were immersed in a sulfuric acid solution at pH 1.8 for 6 hours and then crushed by means of a household disposer (pH: 4.2), followed by adding commercially available maceration enzymes 1 g (containing per 1 g, 1,440 units of pectin endopolygalacturonase, 990 units of carboxy methyl cellulase, 390 units of arabinoxylanase, and 315 units of arabinogalactanase), and reaction in a 2 l capacity stainless steel vessel with stirrings sometimes at 45° C. for one hour to obtain a macerated material. Sodium hydroxide was then added to the macerated material to adjust the pH to 5.6. A bacterial α-amylase preparation (3,500 units/g) (0.5 g) was then added followed by dextrinization reaction in a 1 l capacity stainless steel separable flask, while continuously injecting the mixture by means of a roller pump and continuously discharging the resulting product, under conditions of a retention time of 10 minutes and 85° C. As a result, the starch (about 28% by weight) contained in the crushed material was dextrinized (percentage dextrinization: 11%), and the concentration of the dextrinized material was nearly 31.0% in terms of glucose after saccharification by glucoamylase. This means that the raw material was never diluted during the dextrinization and saccharification process; hence it is possible to subject the resulting material as it is to the subsequent alcohol fermentation.

To the dextrinized material (liquid) were added per 1 kg, 12.5 g of a yeast seed for alcohol fermentation (SACCHAROMYCES CEREVISIAE HANSEN RASSE XII), and as mineral nutrients for the yeast, 1.1 g of potassium dihydrogen phosphate, 1.5 g of ammonium sulfate, 0.13 g of magnesium sulfate and 0.13 g of calcium chloride, and 1 g of glucoamylase (1,200 units of active glucoamylase per 1 g thereof), followed by fermentation in a small type fermenter (5 l capacity) at pH 4.5 and 25° C. As a result, the alcohol concentration amounted to 16.9% by volume in 43 hours; thus a high concentration alcohol fermentation was achieved in a short time.

EXAMPLE 2

Two kg of washed white potato were immersed in a sulfuric acid solution at pH 1.8 for 6 hours and then crushed by means of a disposer, followed by adding 0.5 g of the same maceration enzymes as used in Example 1. The mixture was placed in a 2 l capacity stainless steel vessel and its pH was adjusted to 4.5 with stirring, followed by keeping it at 45° C. for one hour to obtain a slurry material, which was then subjected to solid-liquid separation by means of a centrifugal decanter. Two thirds of the resulting supernatant liquid (about 520 ml from 1 kg of potato) was removed. Sodium hydroxide was then added to the residue with stirring to adjust the pH to 5.6, followed by adding 0.5 g of the same bacterial α-amylase as used in Example 1 to the mixture and subjecting it to dextrinization reaction in a 1 l capacity stainless steel separrable flask, while repeating on operation of continuously injecting the mixture by means of a roller pump and continuously discharging the resulting material, under conditions of a retention time of 5 minutes and 88° C. As a result, the percentage dextrinization relative to the raw material was 12%, and the total sugar content of the dextrinzed material was 32%; thus it was possible to prepare a dextrinized liquid which was more concentrated by about 60% than that obtained by cooking potato followed by dextrinization by the bacterial α-amylase.

To the dextrinization liquid thus prepared were then added, as in Example 1, per 1 kg of the liquid, 12 g of a yeast seed for alcohol fermentation (S. CEREVISIAE R. XII), 1 g of glucoamylase, and as mineral nutrients, 1.1 g of potassium dihydrogen phosphate, 1.5 g of ammonium sulfate, 0.13 g of magnesium sulfate and 0.13 g of calcium chloride, followed by subjecting the mixture to fermentation in a small type fermenter at pH 4.5 and 25° C. The resulting alcohol concentration amounted to 16.7% by volume in 44 hours; thus it was possible to achieve a high concentration alcohol fermentation which had been impossible according to the conventional process, by the use of white potato as raw material and in a very short time.

Even when raw cassava was used as raw material, almost the same results were obtained.

EXAMPLE 3

One kg of sweet potato as raw material was immersed in a dilute hydrochloric acid at pH 1.8 for 4 hours and just thereafter crushed and triturated by means of a disposer, followed by adding 0.05% by weight based on the weight of the raw material, of maceration enzyme agent (containing per 1 g thereof, 990 units of carboxy methyl cellulase, 315 units of arabinogalactanase, 390 units of arabinoxylanase, 1,440 units of pectin endopolygalacturanase and 69 units of acidically active α-amylase) and 0.1% by weight of glucoamylase which is of Rhizopus origin and containing 2,510 units of glucoamylase per 1 g), and then subjecting the mixture to reaction in a 2 l capacity stainless steel vessel with stirring at pH 4.8 and 40° C. As a result, the triturated material of the raw sweet potato was decomposed to become a slurry in a few hours, and when the mixture was further incubated under the same conditions, saccharification of the starch proceeded in three days ultimately to reach the reducing sugar formation corresponding to the hydrolysis degree of 50% or more of the starch.

To this mixture but immediately after adding glucoamylase were added a yeast seed for alcohol fermentation (0.12 g as dry weight) and as mineral nutrients for the yeast, a mixture consisting of 0.25 g of potassium dihydrogen phosphate ($KH_2PO_4$), 0.6 g of ammonium sulfate (($NH_4)_2SO_4$) and 0.07 g of magnesium sulfate ($MgSO_4.7H_2O$) (pH: 4.0), and the resulting mixture was kept at 23° C. for 6 days, followed by distilling the whole and then determing ethanol volume in the resulting distillate, to give an ethanol yield per 1 kg of the raw material (sweet potato), of 146 ml in terms of anhydrous ethanol. This yield is similar to that in the case where the same raw sweet potato was conventionally cooked and then saccharified, followed by alcohol fermentation, but when it is taken into consideration that the consumption of the energy required for the above cooking (about 30% of the total energy required for ethanol production) was saved, it can be seen that the present invention is practically valuable.

Further, the above procedure was repeated except that the raw sweet potato as raw material was replaced by raw cassava, to give almost the same results.

EXAMPLE 4

One kg of raw sweet potato was subjected to acid treatment and then crushed and triturated as in Example 3, followed by adding 0.05% by weight of commercially available maceration enzymes A (containing per 1 g, 980 units of cellulase, 330 units of arabinogalactanase, 360 units of arabinoxylanase, 280 units of pectin endopolygalacturonase and 65 units of an acidically active α-amylase), 580 units of pectin endopolygalacturonase isolated from the maceration enzyme as used in Example 3, per 1 kg of raw sweet potato, and 0.1% by weight of glucoamylase (of Rhizopus origin and containing 2,510 units of glucoamylase per 1 g thereof), and then subjecting the mixture of alcohol fermentation by adding a yeast seed. As a result, the ethanol yield in terms of anhydrous ethanol after fermentation for 7 days and distillation was 144 ml per 1 kg of raw material sweet potato.

When the same procedure as the above was repeated except that pectin endopolygalacturonase (580 units/kg raw roots) was not added, the ethanol yield in terms of anhydrous ethanol after alcohol fermentation was 101 ml per 1 kg of sweet potato.

EXAMPLE 5

In place of maceration enzymes of Example 3, using 0.05% by weight of commercially available maceration enzymes B (containing per 1 kg, 1,000 units of cellulase, 75 units of arabinogalactanase, 85 units of arabinoxylanase, 2,100 units of pectin endopolygalacturonase and 90 units of an acidically active α-amylase) to which was further added arabinogalactanase (120 units) and arabinoxylanase (152 units) both separated from the former maceration enzymes (these units being lesser than those in the former maceration enzymes), decomposition through maceration and saccharification, and subsequent alcohol fermentation as in Example 3 were carried out. As a result, the ethanol yield (as an anhydrous ethanol) after fermentation and distillation was 145 ml per 1 kg of raw sweet potato.

In addition, when the above enzymes B alone were used (that is, arbinogalactanase and arabinoxylanase were not further added), the ethanol yield per 1 kg of sweet potato was 105 ml.

EXAMPLE 6

Ten kg of raw sweet potato were immersed in a hydrochloric acid solution and then crushed and triturated by means of a disposer in the same manner as in Example 3, followed by adding a mixture consisting of 0.05% of the same maceration enzymes as in Example 3, 1.2 g of a yeast for alcohol fermentation based on the dry weight thereof, 2.5 g of potassium dihydrogen phosphate ($KH_2PO_4$), 6 g of ammonium sulfate (($NH_4)_2SO_4$) and 0.7 g of magnesium sulfate ($MgSO_4.7H_2O$) as mineral nutrients (pH: 4.6), and then keeping the mixture at 15° to 25° C. for 5 days, after which the whole of the resulting fermented beer was subjected to distillation and the ethanol quantity in the distillate was determined, to give an ethanol yield (as an anhydrous ethanol) of 1,450 ml per 10 kg of the raw sweet potato.

What is claimed is:

1. A process for saccharification of rootstocks and subsequent alcohol fermentation, which process comprises:
   a step of immersing rootstocks in a dilute acid solution to sterilize them;
   a step of crushing the resulting sterilized rootstocks;
   a step of macerating the crushed rootstocks through the action of macerating enzymes composed mainly of a polygalacturonase;
   a step of forming a slurry comprising liquid and starch derived solely from the product resulting from the action of said macerating enzymes on the crushed rootstocks;
   a step of adding a bacterial α-amylase to the resulting slurry to dextrinize the starch contained therein; and
   a step of adding to the resulting dextrinized starch, glucoamylase as a saccharifying enzyme, and yeast for alcohol fermentation to effect saccharification and alcohol fermentation.

2. A process according to claim 1 wherein said rootstocks are at least one selected from the group consisting of white potatoes, sweet potatoes and cassava roots.

3. A process according to claim 1 wherein said polygalacturonase is pectin endopolygalacturonase.

4. A process according to claim 3 wherein said maceration enzymes contain small amounts of carboxymethylcellulase, arabinoxylanase and arabinogalactanase, in addition to said pectin endopolygalacturonase.

5. A process according to claim 1 wherein said dextrinizing step by a bacterial α-amylase is carried out at temperature of 80° C. to 90° C. and at pH of 5 or higher.

6. A process according to claim 1 wherein said maceration step by said maceration enzymes is carried out at temperature of 20° C. to 45° C. and at pH of 3.5 to 5.0.

7. A process according to claim 1 wherein said dilute acid is an aqueous solution of at least one compound selected from the group consisting of hydrochloric acid, sulfuric acid, and nitric acid.

8. A process according to claim 7, wherein the concentration of the acid is in the range of 0.02 to 0.08 normality.

9. A process according to claim 1 wherein a portion of the liquid in the slurry is removed before the dextrinizing step.

10. A process according to claim 9, wherein said rootstocks as raw material are white potatoes.

11. A process according to claim 1, wherein said dilute acid is an aqueous solution of acetic acid.

12. A process according to claim 11, wherein the concentration of the acid is in the range of 0.04 to 0.10 normality.

13. A process according to claim 1, wherein the rootstock is at least one of white potatoes and cassava root and the maceration enzymes are added in the ratio of 5 to 200 units per 100 g. of rootstocks.

14. A process according to claim 1, wherein the rootstock is sweet potatoes and the maceration enzymes are added in the ratio of 50 to 1,000 units per 100 g. of rootstocks.

15. A process according to claim 1, wherein the maceration step is conducted for 0.5 to 1 hour and the dextrinization step is conducted for about 1 to 15 minutes.

16. A process according to claim 1, wherein 4 to 16 units per gram of starch of bacterial α-amylase is added.

17. A process according to claim 1, wherein the saccharification and alcohol fermentation step is conducted at 25° C. and at a pH of 4.5.

18. A process according to claim 1, wherein 2 to 10 units per gram of starch of the saccharifying enzyme are added.

19. A process according to claim 1, wherein small amounts of ammonium sulfate, potassium dihydrogen phosphate, calcium chloride and magnesium sulfate are added as nutrients for the yeast.

20. A batch process for saccharification of rootstocks and subsequent alcohol fermentation, which process comprises:
   a step of immersing rootstocks in a dilute acid solution to sterilize them;
   a step of crushing the resulting sterilized rootstocks;
   a step of macerating the crushed rootstocks through the action of blended enzyme agents comprising cellulase, hemicellulase, pectin endopolygalacturonase, glucoamylase and acidically active α-amylase;
   a step of forming a slurry comprising liquid and starch derived solely from the product resulting from the action of said blended enzymes on the crushed rootstocks;
   a step of adding yeast for alcohol fermentation to the slurry to effect alcohol fermentation.

21. A process according to claims 1 or 20, wherein the pH of the dilute acid solution is in the range of 1.6 to 2.8.

22. A process according to claims 1 or 20, wherein the rootstocks are immersed in the dilute acid solution for a period of approximately 4 to 6 hours.

23. A process according to claims 1 to 10, wherein the rootstocks are crushed into particles having a size in the range of 8 to 20 meshes.

24. A process according to claim 20 wherein said rootstocks are selected from the group consisting of sweet potatoes and casava roots.

25. A process according to claim 20 wherein said blended enzyme agents are composed mainly of maceration enzymes and starch saccharifying amylase.

26. A process according to claim 20 wherein said blended enzyme agents contain per kg of rootstocks, 300 units or more of carboxymethylcellulase as said cellulase, 100 units or more of arabinoxylanase as said hemicellulase, as 100 units or more of said arabinogalactanase, 400 units or more of said pectin endopolygaracturonase in terms of a pectin viscosity-lowering activity, 1,500 units or more of said glucoamylase in terms of a starch-saccharifying activity, and 20 units or more of said acidically active α-amylase in terms of a starch-gelatinizing activity determined by the iodometric method.

27. A process according to claim 20 wherein said maceration and saccharification of root-stocks by the action of said blended enzyme agents are carried out at temperature of 20° to about 45° C. and at pH of 3.5 to 5.0.

28. A process according to claim 27, wherein the temperature is 20° to 35° C.

29. A process according to claim 20 wherein said alcohol fermentation step is carried out at the same time with said maceration and saccharification step.

30. A process according to claim 20 wherein said blended enzyme agents are enzymes produced by fungi.

31. A process according to claim 30, wherein said fungi are selected from the group consisting of genus Aspergillus and genus Rhizopus.

32. A process according to claim 31, wherein the fungus is *Aspergillus niger*.

33. A batch for saccharification of rootstocks and subsequent alcohol fermentation comprising:
 (a) immersing the rootstocks in a dilute acid to sterilize them;
 (b) crushing the sterilized rootstocks from (a);
 (c) macerating the crushed rootstocks from (b) through the action of macerating enzymes;
 (d) forming a slurry comprising liquid and starch derived solely from the product resulting from the action of said macerating enzymes on the crushed rootstocks;
 (e) dextrinizing the starch from (d) through the action of dextrinizing enzymes;
 (f) saccharifying and fermenting the dextrinized starch from (d) through the action of a saccharifying enzyme and an alcohol fermentation yeast to effect saccharification and alcohol fermentation.

34. A process for the saccharification of white potatoes and subsequent alcohol fermentation comprising:
 (a) immersing the white potatoes in a dilute acid to sterilize them;
 (b) crushing the white potatoes from (a);
 (c) macerating the crushed white potatoes through the action of macerating enzymes composed mainly of a polygalacturonase;
 (d) a step of forming a slurry comprising liquid and starch derived solely from the product resulting from the action of said macerating enzymes on the crushed rootstocks;
 (e) removing a portion of the liquid produced in (c);
 (f) dextrinizing the starch from (c) through the action of bacterial α-amylase;
 (g) saccharifying and fermenting the dextrinized starch from (f) through the action of glucoamylase and an alcohol fermentation yeast to effect saccharification and alcohol fermentation respectively.

* * * * *